(12) United States Patent
Nishigaki

(10) Patent No.: US 11,882,377 B2
(45) Date of Patent: Jan. 23, 2024

(54) CONTROL DEVICE, MEDICAL OBSERVATION SYSTEM, CONTROL METHOD, AND COMPUTER READABLE RECORDING MEDIUM

(71) Applicant: Sony Olympus Medical Solutions Inc., Tokyo (JP)

(72) Inventor: Yasuhiro Nishigaki, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 17/505,624

(22) Filed: Oct. 20, 2021

(65) Prior Publication Data

US 2022/0256125 A1    Aug. 11, 2022

(30) Foreign Application Priority Data

Feb. 9, 2021    (JP) .................................. 2021-019386

(51) Int. Cl.
| | | |
|---|---|---|
| *H04N 7/52* | (2011.01) | |
| *H04N 7/171* | (2011.01) | |
| *H04N 7/083* | (2006.01) | |
| *H04N 7/01* | (2006.01) | |
| *H04N 7/085* | (2006.01) | |
| *H04N 7/084* | (2006.01) | |

(Continued)

(52) U.S. Cl.
CPC ........... *H04N 5/04* (2013.01); *A61B 1/00009* (2013.01); *A61B 1/04* (2013.01); *H04N 5/12* (2013.01); *H04N 5/935* (2013.01); *H04N 7/0115* (2013.01); *H04N 7/083* (2013.01); *H04N 7/084* (2013.01); *H04N 7/085* (2013.01); *H04N 7/1716* (2013.01); *H04N 7/52* (2013.01); *H04N 7/56* (2013.01)

(58) Field of Classification Search
CPC ........ H04N 7/083; H04N 7/084; H04N 7/085; H04N 5/04; H04N 5/12; H04N 5/935; H04N 7/56

See application file for complete search history.

(56) References Cited

U.S. PATENT DOCUMENTS 5,896,164 A * 4/1999 Orbach .................. A61B 5/486
                                                                    386/230
6,441,812 B1 * 8/2002 Voltz ...................... H04N 5/073
                                                                    348/544

(Continued)

FOREIGN PATENT DOCUMENTS

EP    871140 A2 * 10/1998 ......... G06K 15/1219
EP    2557774 A1 * 2/2013 ......... A61B 1/00006

(Continued)

*Primary Examiner* — David N Werner
(74) *Attorney, Agent, or Firm* — XSENSUS LLP

(57) ABSTRACT

A control device includes: generation circuitry configured to output a field signal to a medical imaging device; first detection circuitry configured to detect a horizontal synchronization signal from video data output from the medical imaging device, the video data including at least the horizontal synchronization signal; and a monitoring circuitry configured to monitor whether or not an abnormality occurs in one frame period of the video data based on a period of the horizontal synchronization signal detected by the first detection circuitry for a predetermined n-th time after polarity of the field signal is switched.

15 Claims, 11 Drawing Sheets

(51) Int. Cl.
*H04N 7/56* (2006.01)
*H04N 5/12* (2006.01)
*H04N 5/935* (2006.01)
*H04N 5/04* (2006.01)
*A61B 1/04* (2006.01)
*A61B 1/00* (2006.01)

(56) References Cited

U.S. PATENT DOCUMENTS

| | | | | |
|---|---|---|---|---|
| 6,583,822 B1* | 6/2003 | Jun | .......................... | H04N 5/04 |
| | | | | 348/E5.017 |
| 2002/0097869 A1* | 7/2002 | Pasqualino | ........ | H04N 21/4342 |
| | | | | 375/E7.274 |
| 2002/0136241 A1* | 9/2002 | Pasqualino | ............. | H03L 7/085 |
| | | | | 375/E7.274 |
| 2002/0158814 A1* | 10/2002 | Bright | .................. | H04N 9/3132 |
| | | | | 348/E9.026 |
| 2006/0264734 A1* | 11/2006 | Kimoto | ............. | A61B 1/00036 |
| | | | | 600/407 |
| 2007/0055099 A1* | 3/2007 | Kimoto | .................. | A61B 1/041 |
| | | | | 600/109 |
| 2007/0132839 A1* | 6/2007 | Pang | ...................... | A61B 1/045 |
| | | | | 348/65 |
| 2007/0274649 A1* | 11/2007 | Takahashi | ............ | A61B 1/0655 |
| | | | | 348/E7.087 |
| 2008/0143876 A1* | 6/2008 | Kouramanis | ............ | H04N 5/04 |
| | | | | 348/553 |
| 2009/0278984 A1* | 11/2009 | Suzuki | ................... | H04N 7/081 |
| | | | | 348/554 |
| 2011/0085081 A1* | 4/2011 | Tsai | ........................ | H04N 5/04 |
| | | | | 348/E5.009 |
| 2014/0320621 A1* | 10/2014 | Sonnenschein | ...... | H04N 5/2257 |
| | | | | 348/294 |
| 2015/0002373 A1* | 1/2015 | Kobayashi | ......... | A61B 5/02438 |
| | | | | 345/8 |
| 2019/0076006 A1* | 3/2019 | Takeda | ................... | A61B 1/045 |
| 2020/0225701 A1* | 7/2020 | Tsao | ...................... | G06F 1/203 |

FOREIGN PATENT DOCUMENTS

| | | | | |
|---|---|---|---|---|
| JP | 2005319097 A | * | 11/2005 | ............. A61B 1/041 |
| JP | 2018-158159 A | | 10/2018 | |
| WO | WO-2005122867 A1 | * | 12/2005 | ......... A61B 1/00188 |
| WO | WO-2012169513 A1 | * | 12/2012 | ............ H04L 7/0331 |
| WO | WO-2013049347 A1 | * | 4/2013 | ......... A61B 1/00009 |

\* cited by examiner

CONTROL DEVICE, MEDICAL OBSERVATION SYSTEM, CONTROL METHOD, AND COMPUTER READABLE RECORDING MEDIUM

CROSS-REFERENCE TO RELATED APPLICATION

This application claims priority from Japanese Application No. 2021-019386, filed on Feb. 9, 2021, the contents of which are incorporated by reference herein in its entirety.

BACKGROUND

The present disclosure relates to a control device, a medical observation system, a control method, and a computer readable recording medium.

In medical endoscope systems, video data including a vertical synchronization signal have been transmitted from endoscopes to control devices (see, e.g., JP 2018-158159 A).

SUMMARY

Meanwhile, in a medical endoscope system such as one in JP 2018-158159 A described above, a vertical synchronization signal included in video data is detected, and it is monitored based on this detection result whether or not there is any periodic disturbance of one frame of the video data.

In addition, some types of medical imaging devices, such as an endoscope and a surgical microscope having an imaging function, do not include a vertical synchronization signal in video data to be transmitted to control devices. Therefore, in a medical imaging device that transmits video data not including a vertical synchronization signal, a control device, such as one in JP 2018-158159 A described above, may not detect a vertical synchronization signal. Therefore, there has been a problem that a disturbance of one frame period of the video data may not be monitored.

According to the present disclosure, there is provided a control device including: generation circuitry configured to output a field signal to a medical imaging device; first detection circuitry configured to detect a horizontal synchronization signal from video data output from the medical imaging device, the video data including at least the horizontal synchronization signal; and a monitoring circuitry configured to monitor whether or not an abnormality occurs in one frame period of the video data based on a period of the horizontal synchronization signal detected by the first detection circuitry for a predetermined n-th time after polarity of the field signal is switched.

DETAILED DESCRIPTION

Figure 1:
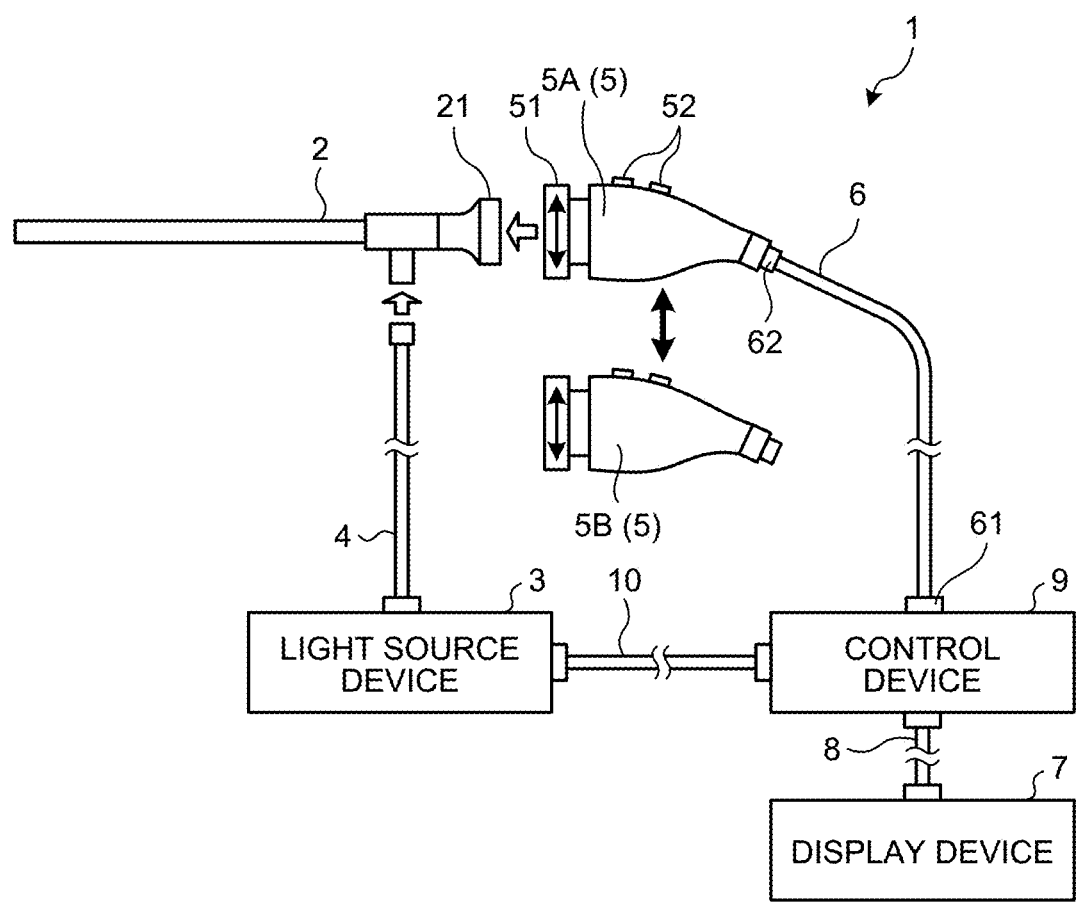
FIG. 1 is a view illustrating a schematic configuration of an endoscope system according to a first embodiment.

Hereinafter, embodiments for carrying out the present disclosure will be described in detail with reference to the drawings. Note that the present disclosure is not limited to the following embodiments. In addition, each drawing to be referred to in the following description merely schematically illustrates shapes, sizes, and positional relationships to an extent that the content of the present disclosure may be understood. That is, the present disclosure is not limited only to the shapes, sizes, and positional relationships illustrated in each drawing. Furthermore, in the illustration of the drawings, the same portions will be denoted by the same reference numerals for description. Still furthermore, as an example of a medical observation system according to the present disclosure, an endoscope system including a rigid endoscope will be described.

First Embodiment

Schematic Configuration of Endoscope System

FIG. 1 is a view illustrating a schematic configuration of an endoscope system according to a first embodiment. An endoscope system 1 illustrated in FIG. 1 is a system that is used in a medical field, is inserted into a living body of a subject such as a living body of a human or an animal, and observes the subject by displaying an image in which the inside is imaged. Note that in the first embodiment, a rigid endoscope system using a rigid endoscope (insertion unit 2) illustrated in FIG. 1 will be described as the endoscope system 1, but the present disclosure is not limited thereto, and for example, a flexible endoscope system may be used.

The endoscope system 1 illustrated in FIG. 1 includes the insertion unit 2, a light source device 3, a light guide 4, a first camera head 5A (endoscope imaging device) and a second camera head 5B (endoscope imaging device) having different image sensor functions from each other, a first transmission cable 6, a display device 7, a second transmission cable 8, a control device 9, and a third transmission cable 10. Note that when one of the first camera head 5A and the second camera head 5B is referred to in the following description, it will be described by being simply denoted by a camera head 5.

The insertion unit 2 is rigid or at least partially flexible and has an elongated shape. The insertion unit 2 is inserted inside a subject such as a patient. The insertion unit 2 is configured using one or more of lenses therein, and is provided with an optical system that combines observation images.

One end of the light guide 4 is connected to the light source device 3. Under the control by the control device 9, the light source device 3 emits (supplies) white light for illuminating the inside of a subject to the one end of the light guide 4, and excitation light or infrared light to a drug administered to or scattered on a subject. The light source device 3 is configured using a light emitting diode (LED) light source or a semiconductor laser element such as a laser diode (LD). The light source device 3 and the control device 9 may be configured to communicate individually as illustrated in FIG. 1, or may be configured to be integrated.

One end of the light guide 4 is detachably connected to the light source device 3, and the other end is detachably connected to the insertion unit 2. The light guide 4 guides light emitted from the light source device 3 from the one end to the other end, and supplies the light to the insertion unit 2.

An eyepiece unit 21 of the insertion unit 2 is detachably connected to the camera head 5. Under the control by the control device 9, the camera head 5 generates video data (image signal) by capturing an observation image formed by the insertion unit 2, and outputs this video data. In addition, the camera head 5 includes an operation ring unit 51 provided to be rotatable in a circumferential direction, and a plurality of input units 52 that receive input of instruction signals for instructing various operations of the endoscope system 1. Note that in the first embodiment, the camera head 5 and the insertion unit 2 function as an endoscope. Furthermore, in the first embodiment, one of the first camera head 5A and the second camera head 5B is connected to the control device 9.

One end of the first transmission cable 6 is detachably connected to the control device 9 via a first connector portion 61, and the other end is connected to the camera head 5 via a second connector portion 62. The first transmission cable 6 transmits video data output from the camera head 5 to the control device 9, and transmits a control signal, a synchronization signal, a clock signal, power, and the like output from the control device 9 to the camera head 5.

The display device 7 may be connected to the control device 9 via the second transmission cable 8, and displays a display image based on the video data processed in the control device 9 under the control by the control device 9.

One end of the second transmission cable 8 is detachably connected to the display device 7, and the other end is detachably connected to the control device 9. The second transmission cable 8 transmits, to the display device 7, a display image that is based on the video data processed in the control device 9.

The control device 9 is configured using a memory and a processor having hardware such as a central processing unit (CPU), a graphics processing unit (GPU), an application specific integrated circuit (ASIC), and a field programmable gate array (FPGA). According to a program recorded in the memory, the control device 9 comprehensively controls operations of the light source device 3, the camera head 5, and the display device 7 via each of the first transmission cable 6, the second transmission cable 8, and the third transmission cable 10. In addition, the control device 9 performs various image processing on the video data input from the camera head 5 via the first transmission cable 6, and outputs the video data to the second transmission cable 8.

One end of the third transmission cable 10 is detachably connected to the light source device 3, and the other end is detachably connected to the control device 9. The third transmission cable 10 transmits the control signal from the control device 9 to the light source device 3.

Detailed Configuration of Control Device

Figure 2:
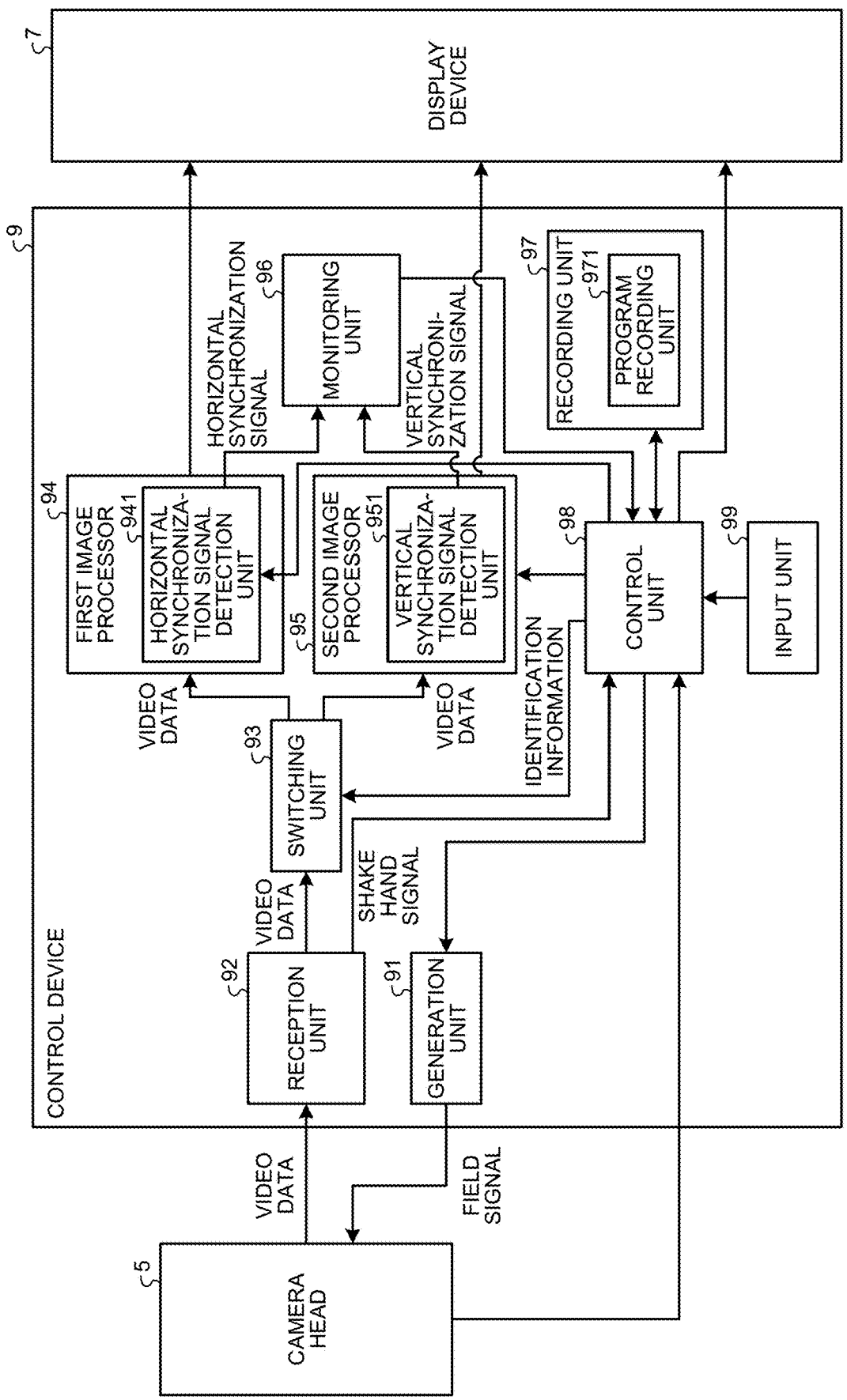
FIG. 2 is a block view illustrating a functional configuration of a control device according to the first embodiment.

Next, a functional configuration of the control device 9 will be described. FIG. 2 is a block view illustrating a functional configuration of the control device 9. Note that a case where the first camera head 5A is connected to the control device 9 will be described below, but the second camera head 5B may also be connected to the control device 9.

The control device 9 illustrated in FIG. 2 includes a generation unit 91, a reception unit 92, a switching unit 93, a first image processor 94, a second image processor 95, a monitoring unit 96, a recording unit 97, a control unit 98, and an input unit 99.

Under the control by the control unit 98, the generation unit 91 generates a field signal that serves as a reference for one field of the video data generated by the camera head 5, and outputs the field signal to the camera head 5. The generation unit 91 is configured using, for example, a timing generator or a clock generator.

Under the control by the control unit 98, the reception unit 92 receives the video data transmitted from the camera head 5, and outputs the received video data to the switching unit 93 and the control unit 98. For example, when the video data transmitted from the camera head 5 are parallel signals, the reception unit 92 is configured using a parallel-serial conversion module and the like that perform parallel-serial conversion processing and the like. In addition, when the video data transmitted from the camera head 5 are optical signals, the reception unit 92 is configured using an O/E conversion module and the like that perform O/E conversion.

One end of the switching unit 93 is electrically connected to the reception unit 92, and the other end is electrically connected to the first image processor 94 or the second image processor 95. Under the control by the control unit 98, the switching unit 93 electrically connects the reception unit 92 and one of the first image processor 94 and the second image processor 95. Specifically, when the first camera head 5A is connected to the control device 9, the switching unit 93 electrically connects the reception unit 92 and the first image processor 94 under the control by the control unit 98. On the other hand, when the second camera head 5B is connected to the control device 9, the switching unit 93 electrically connects the reception unit 92 and the second image processor 95 under the control by the control unit 98. The switching unit 93 is configured using, for example, a semiconductor switch.

Under the control by the control unit 98, the first image processor 94 performs predetermined image processing on the video data input from the switching unit 93, and outputs the video data to the display device 7. Here, the predetermined image processing is, for example, complementary processing or white balance adjustment processing. The first image processor 94 is configured using, for example, a memory and a processor having hardware of an FPGA, a GPU or the like. In addition, the first image processor 94 has a horizontal synchronization signal detection unit 941.

The horizontal synchronization signal detection unit 941 detects a horizontal synchronization signal included in the video data, and outputs this detection result to the monitoring unit 96. Note that in the first embodiment, the horizontal synchronization signal detection unit 941 functions as a first detection unit.

Under the control by the control unit 98, the second image processor 95 performs predetermined image processing on the video data input from the switching unit 93, and outputs the video data to the display device 7. The second image processor 95 is configured using a memory and a processor having hardware such as an FPGA or a GPU. In addition, the second image processor 95 has a vertical synchronization signal detection unit 951.

The vertical synchronization signal detection unit 951 detects a vertical synchronization signal included in the video data, and outputs this detection result to the monitoring unit 96. Note that in the first embodiment, the vertical synchronization signal detection unit 951 functions as a second detection unit.

Under the control by the control unit 98, the monitoring unit 96 monitors whether or not an abnormality occurs in one frame period corresponding to the video data based on a period of the horizontal synchronization signal detected by the horizontal synchronization signal detection unit 941 for a predetermined n-th time after polarity of the field signal input from the generation unit 91 is switched. Specifically, the monitoring unit 96 monitors whether or not an abnormality occurs in one frame period corresponding to the video data based on a period of the horizontal synchronization signal detected by the horizontal synchronization signal detection unit 941 for the first time after the polarity of the field signal input from the generation unit 91 is switched, and outputs this monitoring result to the control unit 98. Furthermore, under the control by the control unit 98, the monitoring unit 96 detects, after recognizing a shake hand signal included in the video data, switching of the polarity of the field signal. In addition, under the control by the control unit 98, the monitoring unit 96 monitors whether or not an abnormality occurs in one frame period corresponding to the video data based on a vertical synchronization signal detected by the vertical synchronization signal detection unit 951 after the polarity of the field signal input from the generation unit 91 is switched, and outputs this monitoring result to the control unit 98. Under the control by the control unit 98, the monitoring unit 96 detects, after recognizing a shake hand signal included in the video data, switching of the polarity of the field signal.

The recording unit 97 records various information on the endoscope system 1 and various data being processed. The recording unit 97 has a program recording unit 971. The program recording unit 971 records various programs to be executed by the endoscope system 1. The recording unit 97 is configured using recording media such as a volatile memory, a non-volatile memory, a hard disk drive (HDD), a solid state drive (SSD), and the like.

The control unit 98 controls each unit constituting the endoscope system 1. The control unit 98 is configured using a memory and a processor having hardware such as a CPU. In addition, the control unit 98 acquires an identification signal (identification information) for identifying the type of the camera head 5, and determines based on the identification signal whether or not a vertical synchronization signal is included in the video data. Thereafter, when a vertical synchronization signal is not included in the video data output from the camera head 5, the control unit 98 causes the switching unit 93 to connect the reception unit 92 and the first image processor 94, thereby causing the switching unit 93 to output the video data to the horizontal synchronization signal detection unit 941 of the first image processor 94. On the other hand, when a vertical synchronization signal is included in the video data output from the camera head 5, the control unit 98 causes the switching unit 93 to connect the reception unit 92 and the second image processor 95, thereby causing the switching unit 93 to output the video data to the vertical synchronization signal detection unit 951 of the second image processor 95. In addition, the control unit 98 detects, from the video data output from the camera head 5, switching of the polarity of each of the shake hand signal and the field signal. Furthermore, when the horizontal synchronization signal detection unit 941 detects the horizontal synchronization signal in a case where the control unit 98 detects switching of the polarity of the field signal after the shake hand signal is detected from the video data, the control unit 98 causes the monitoring unit 96 to monitor one frame period of the video data. On the other hand, when the vertical synchronization signal detection unit 951 detects the vertical synchronization signal after the shake hand signal is detected from the video data, the control unit 98 causes the monitoring unit 96 to monitor one frame period of the video data.

The input unit 99 is configured using a mouse, a keyboard, a touch panel, and the like, receives an input of an instruction signal according to an operation by an operator, and outputs the received instruction signal to the control unit 98.

Outline of Video Data Format

Figure 3:
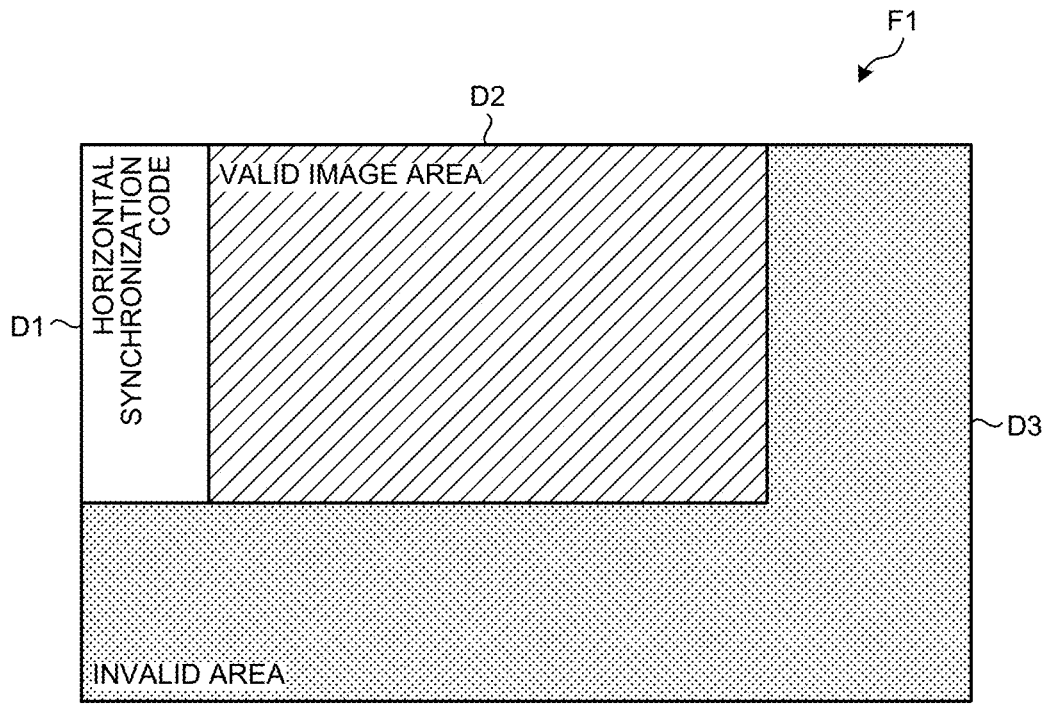
FIG. 3 is a view for explaining an outline of a video data format generated by a first camera head according to the first embodiment.

Next, a video data format generated by each of the first camera head 5A and the second camera head 5B will be described. First, the video data format generated by the first camera head 5A will be described. FIG. 3 is a view for explaining an outline of the video data format generated by the first camera head 5A.

As illustrated in FIG. 3, a video data format F1 generated by the first camera head 5A has a horizontal synchronization code D1, a valid image area D2, and an invalid area D3. The horizontal synchronization code D1 has the horizontal synchronization signal. The valid image area D2 has at least video data in a valid image area of an image sensor, the shake hand signal, and image correction data. The invalid area D3 has at least various information on an image sensor and black correction data to be transmitted during a blanking period.

That is, the video data format F1 generated by the first camera head 5A includes no vertical synchronization signal. Therefore, known medical observation systems may not detect a vertical synchronization signal for the video data format F1, so that a disturbance of one frame period, that is, an abnormality in one frame period may not be monitored.

Figure 4:
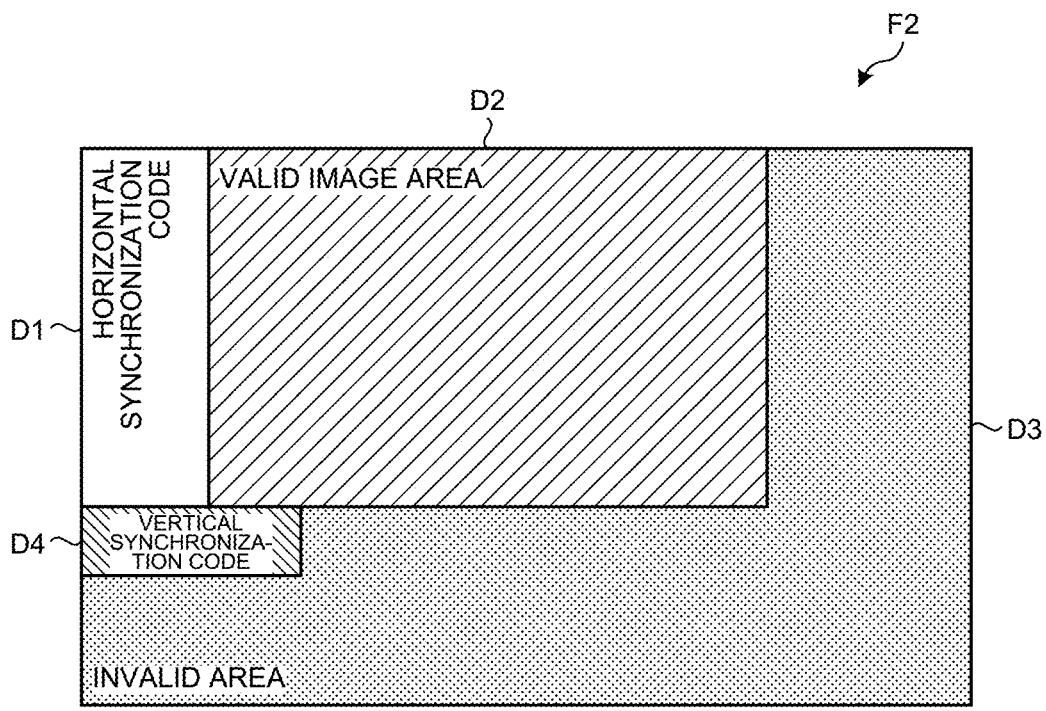
FIG. 4 is a view for explaining an outline of another video data format generated by a second camera head according to the first embodiment.

Next, a video data format generated by the second camera head 5B will be described. FIG. 4 is a view for explaining an outline of the video data format generated by the second camera head 5B.

As illustrated in FIG. 4, a video data format F2 generated by the second camera head 5B has the horizontal synchronization code D1, the valid image area D2, and the invalid area D3. Furthermore, the invalid area D3 has a vertical synchronization code D4 in which the vertical synchronization signal is embedded. Therefore, known medical observation systems may monitor a disturbance of one frame period, that is, an abnormality in one frame period by monitoring the vertical synchronization signal.

Processing Upon Connection of First Camera Head

Figure 5:
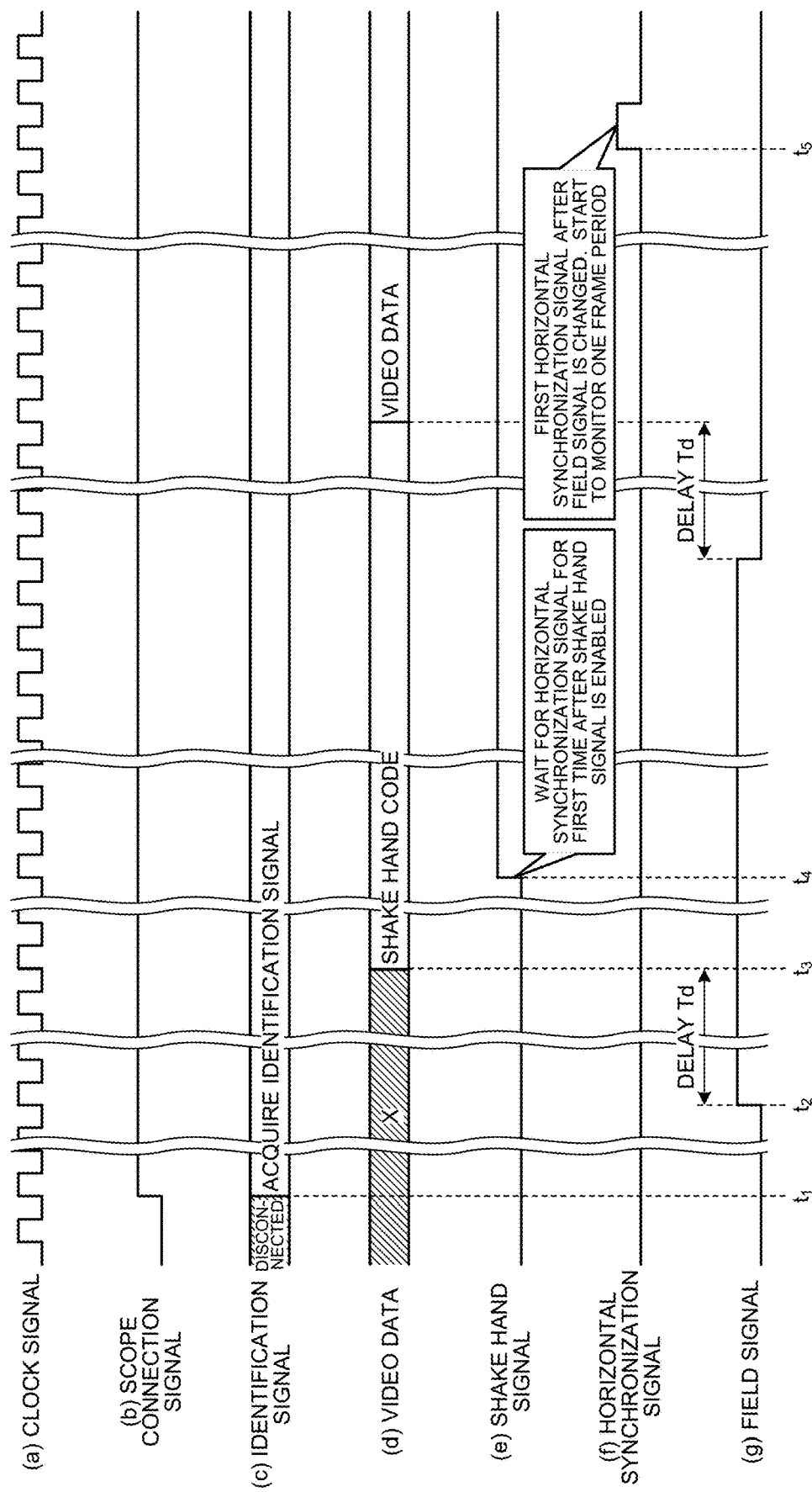
FIG. 5 is a view illustrating timing charts when the first camera head according to the first embodiment is connected.

Next, processing when the first camera head 5A is connected to the control device 9 will be described. FIG. 5 is a view illustrating timing charts when the first camera head 5A is connected. Note that in FIG. 5, a monitoring start timing of one frame period will be described. From the top in FIG. 5, (a) indicates the clock signal, (b) indicates a scope connection signal, (c) indicates the identification signal, (d)

indicates the video data, (e) indicates the shake hand signal, (f) indicates the horizontal synchronization signal, and (d) indicates the field signal.

As illustrated in FIG. 5, when the first camera head 5A is connected to the control device 9 and the scope connection signal is received from the first camera head 5A, the control unit 98 first acquires the scope type identification signal from the first camera head 5A according to the clock signal (time $t_1$).

Subsequently, after the polarity of the field signal from the generation unit 91 is switched, that is, when the field signal rises (time $t_2$), the control unit 98 detects a shake hand code included in the video data transmitted from the first camera head 5A (time $t_3$).

Thereafter, the control unit 98 enables the shake hand signal (sets the state of the pulse to a HIGH state) (time $t_4$) when a predetermined time (e.g., delay Td) elapses from the rising of the field signal (the state of the pulse is a HIGH state).

Subsequently, the control unit 98 causes the monitoring unit 96 to stand by until the first horizontal synchronization signal is detected by the horizontal synchronization signal detection unit 941 (time $t_5$) after the shake hand signal is enabled (time $t_4$).

Figure 6:
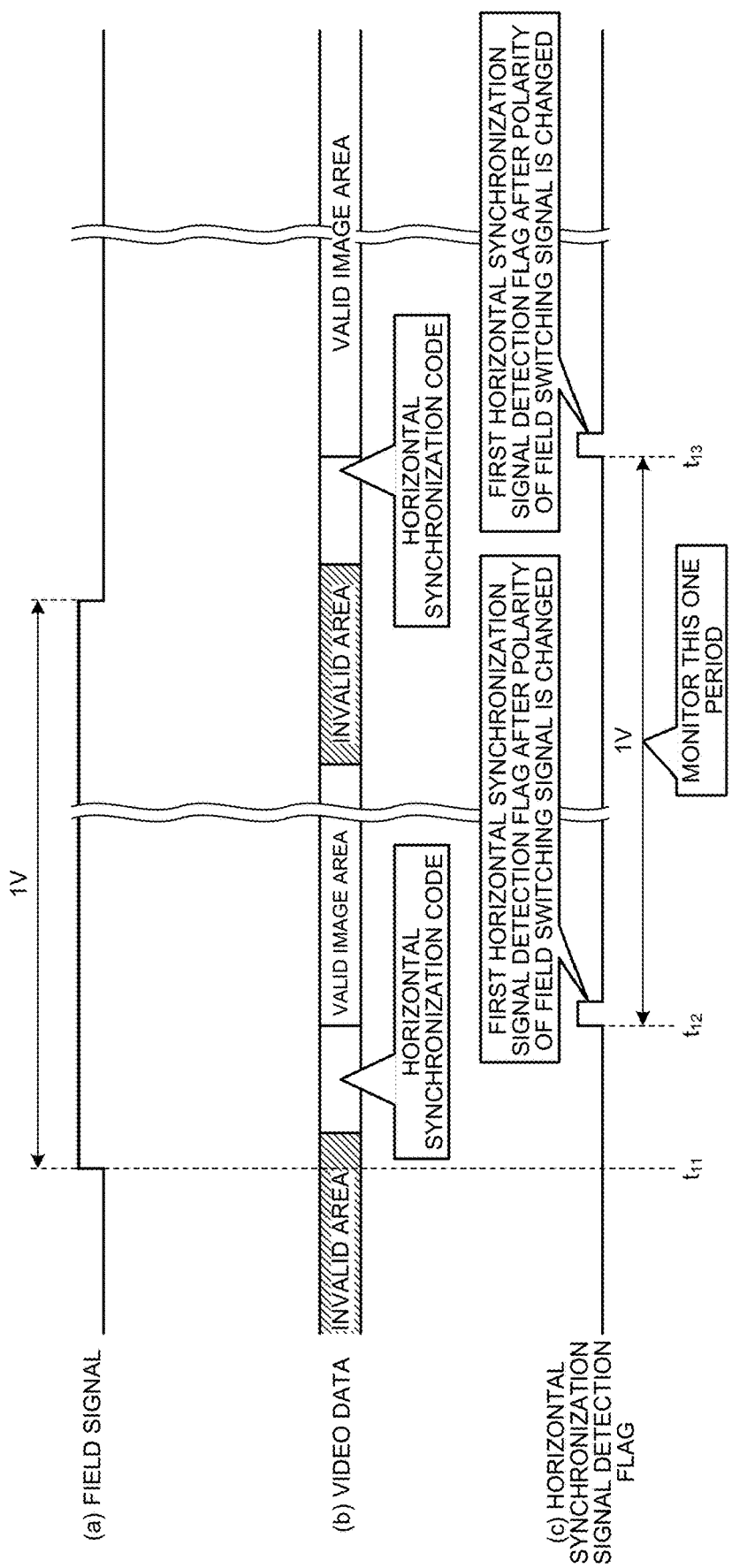
FIG. 6 is a view illustrating a timing of a horizontal synchronization signal to be monitored according to the first embodiment.

FIG. 6 is a view illustrating a timing of the horizontal synchronization signal to be monitored. From the top in FIG. 6, (a) indicates the field signal, (b) indicates the video data, and (c) indicates a timing at which the horizontal synchronization signal is detected.

As illustrated in FIG. 6, the control unit 98 causes the monitoring unit 96 to monitor by assuming that a period from a detection timing (time $t_{12}$) at which the horizontal synchronization signal detection unit 941 detects the first horizontal synchronization signal after the polarity of the field signal changes (time $t_{11}$) to a detection timing (time $t_{13}$) at which the horizontal synchronization signal detection unit 941 next detects the second horizontal synchronization signal is one frame period (=one field (1 V)). As a result, the monitoring unit 96 may detect a disturbance of the one frame period, that is, an abnormality in the one frame period, even when only the horizontal synchronization signal is included in the video data generated by the first camera head 5A.

Processing Upon Connection of Second Camera Head

Figure 7:
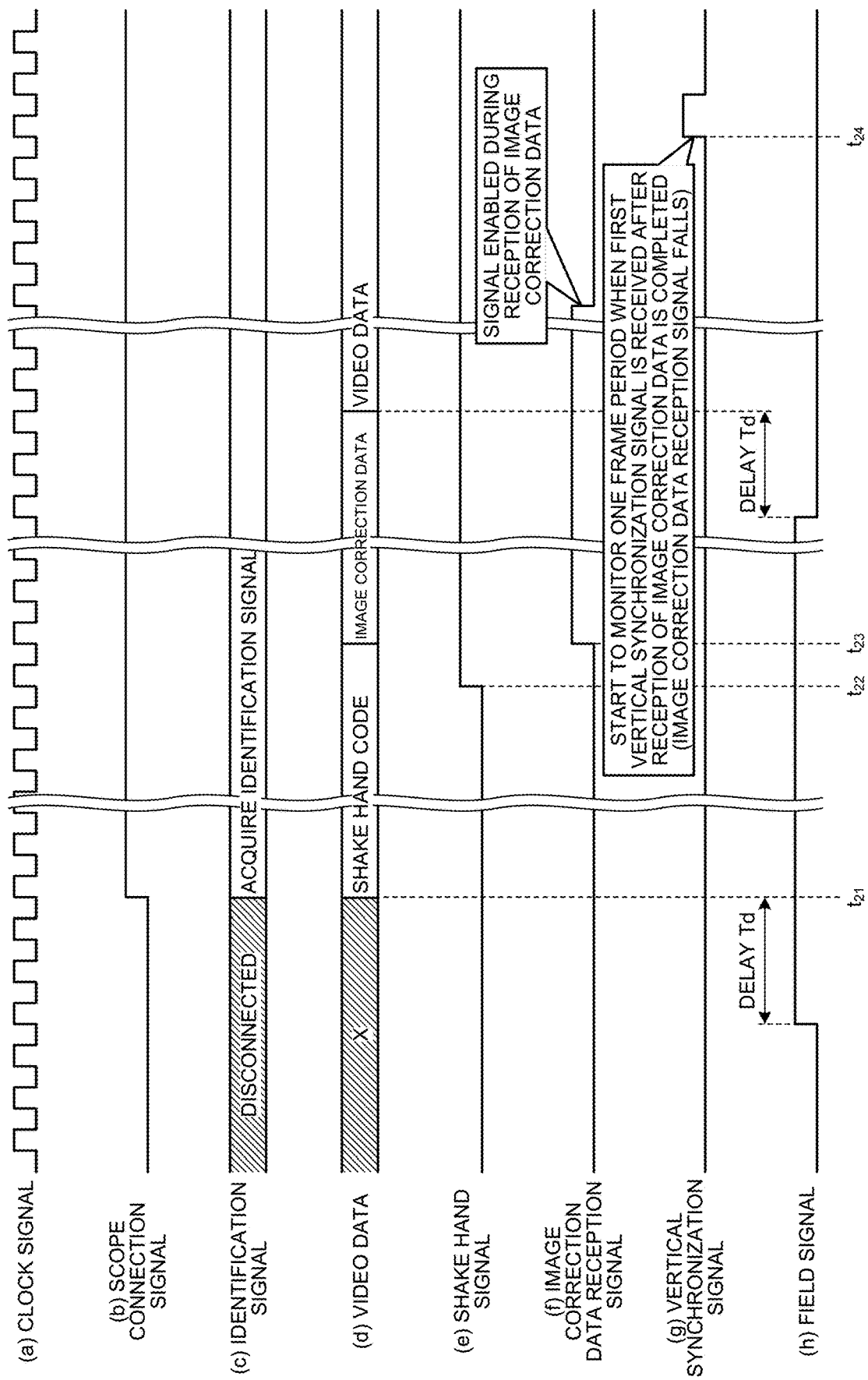
FIG. 7 is a view illustrating timing charts when the second camera head according to the first embodiment is connected.

Next, processing when the second camera head 5B is connected to the control device 9 will be described. FIG. 7 is a view illustrating timing charts when the second camera head 5B is connected. Form the top in FIG. 7, (a) indicates the clock signal, (b) indicates the scope connection signal, (c) indicates the identification signal, (d) indicates the video data, (e) indicates the shake hand signal, (f) indicates an image correction data reception signal, (g) indicates the vertical synchronization signal, and (h) indicates the field signal.

As illustrated in FIG. 7, when the second camera head 5B is connected to the control device 9 and the scope connection signal is received from the second camera head 5B, the control unit 98 first acquires the identification signal from the second camera head 5B according to the clock signal (time $t_n$).

Subsequently, the control unit 98 enables the shake hand signal (sets the state of the pulse to a HIGH state) (time $t_{22}$) when a predetermined time (e.g., delay Td) elapses from the rising of the field signal (the state of the pulse is a HIGH state).

Thereafter, the control unit 98 causes the monitoring unit 96 to monitor one frame period from a timing (time $t_{24}$) at which the vertical synchronization signal detection unit 951 detects the first vertical synchronization signal after the shake hand signal is enabled (time $t_{22}$) and after a timing (time $t_{23}$) at which the image correction data signal rises.

As described above, the monitoring unit 96 may monitor the one frame period based on the vertical synchronization signal included in the video data of the second camera head 5B.

Processing by Control Device

Figure 8:
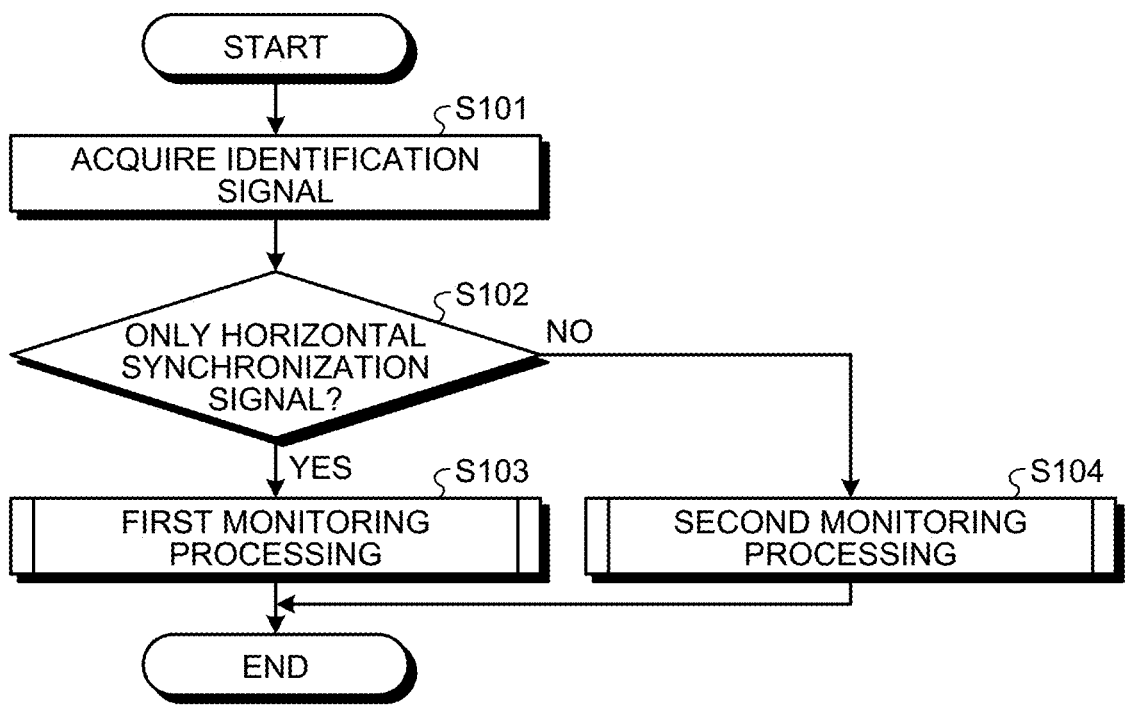
FIG. 8 is a flowchart indicating an outline of processing executed by the control device according to the first embodiment.

Next, processing executed by the control device 9 will be described. FIG. 8 is a flowchart indicating an outline of the processing executed by the control device 9.

As illustrated in FIG. 8, when the camera head 5 is connected to the control device 9, the control unit 98 first acquires an identification signal indicating the type of the camera head 5 from the camera head 5 (step S101).

Subsequently, the control unit 98 determines based on the identification signal acquired from the camera head 5 whether or not the video data transmitted by the camera head 5 includes only the horizontal synchronization signal as a synchronization signal (step S102). Specifically, the control unit 98 determines whether or not the camera head 5 connected to the control device 9 is the first camera head 5A that transmits the video data in the video data format F1 including only the horizontal synchronization signal. When the control unit 98 determines that the video data transmitted by the camera head 5 includes only the horizontal synchronization signal as the synchronization signal (step S102: Yes), the control device 9 proceeds to a step S103 described later. On the other hand, when the control unit 98 determines that the video data transmitted by the camera head 5 includes not only the horizontal synchronization signal as the synchronization signal (step S102: No), the control device 9 proceeds to a step S104 described later.

In the step S103, the control device 9 executes first monitoring processing for determining based on the horizontal synchronization signal included in the video data whether or not an abnormality occurs in one frame period corresponding to the video data. After the step S103, the control device 9 ends the present processing. Note that details of the first monitoring processing will be described later.

In the step S104, the control device 9 executes second monitoring processing for determining based on the vertical synchronization signal included in the video data whether or not an abnormality occurs in one frame period corresponding to the video data. After the step S104, the control device 9 ends the present processing. Note that details of the second monitoring processing will be described later.

First Monitoring Processing

Figure 9:
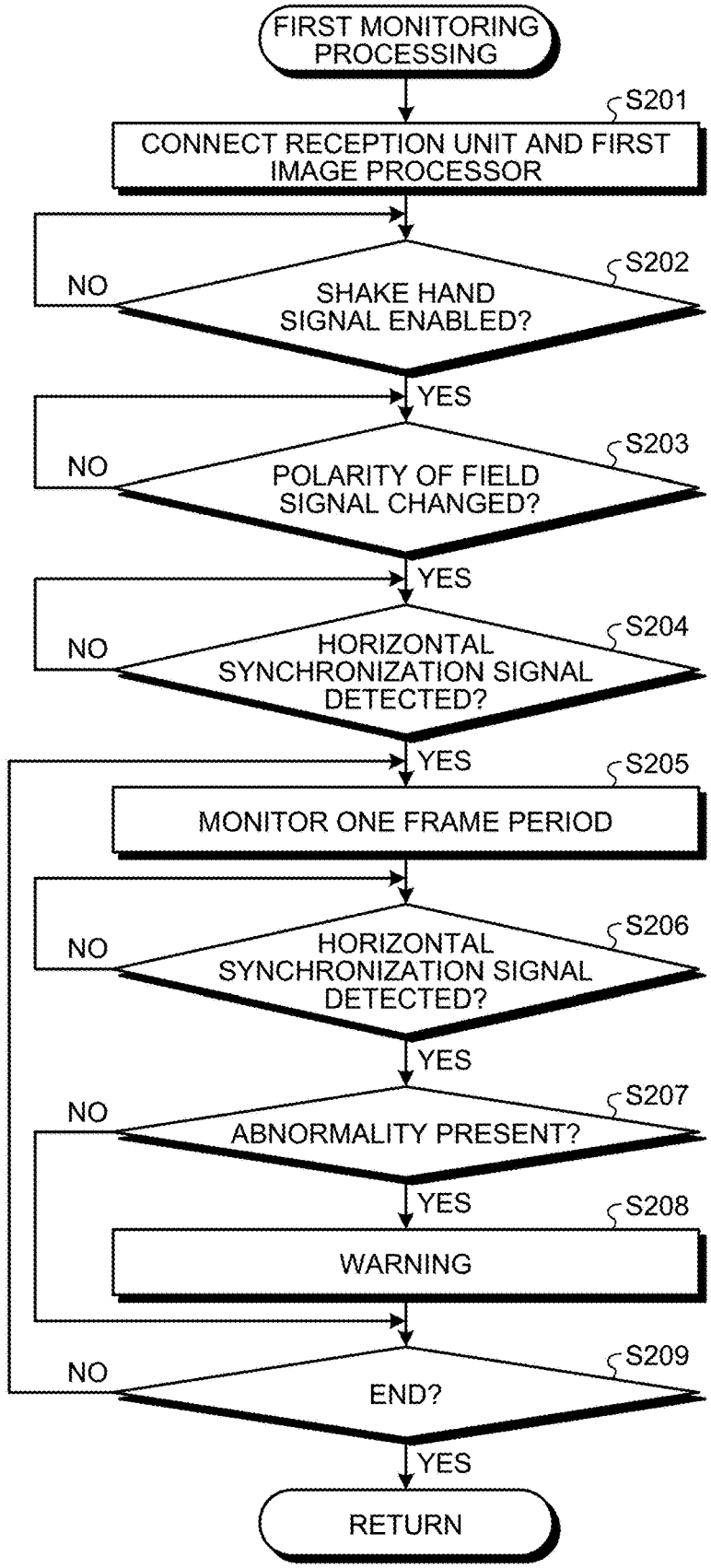
FIG. 9 is a flowchart indicating an outline of first monitoring processing of FIG. 8.

Next, details of the first monitoring processing described in the step S103 of FIG. 8 will be described. FIG. 9 is a flowchart indicating an outline of the first monitoring processing. Note that in FIG. 9, processing when the first camera head 5A is connected to the control device 9 will be described.

As illustrated in FIG. 9, the control unit 98 first connects the reception unit 92 and the first image processor 94 by controlling the switching unit 93 (step S201).

Subsequently, the control unit 98 determines based on the shake hand signal included in the video data output from the reception unit 92 whether or not the shake hand signal is enabled (step S202). When the control unit 98 determines that the shake hand signal is enabled (step S202: Yes), the control device 9 proceeds to a step S203 described later. On the other hand, when the control unit 98 determines that the shake hand signal is not enabled (step S202: No), the control device 9 continues this determination until the shake hand signal is enabled.

In the step S203, the control unit 98 determines whether or not the polarity of the field signal generated by the generation unit 91 has changed. When the control unit 98 determines that the polarity of the field signal generated by the generation unit 91 has changed (step S203: Yes), the control device 9 proceeds to a step S204 described later. On the other hand, when the control unit 98 determines that the polarity of the field signal generated by the generation unit 91 has not changed (step S203: No), the control device 9 continues this determination until the polarity of the field signal changes.

In the step S204, the control unit 98 determines whether or not the horizontal synchronization signal detection unit 941 has detected the horizontal synchronization signal from the video data transmitted from the first camera head 5A. When the control unit 98 determines that the horizontal synchronization signal detection unit 941 has detected the horizontal synchronization signal from the video data transmitted from the first camera head 5A (step S204: Yes), the control device 9 proceeds to a step S205. On the other hand, when the control unit 98 determines that the horizontal synchronization signal detection unit 941 has not detected the horizontal synchronization signal from the video data transmitted from the first camera head 5A (step S204: No), the control device 9 continues this determination until the horizontal synchronization signal detection unit 941 detects the horizontal synchronization signal from the video data.

In the step S205, the control unit 98 causes the monitoring unit 96 to monitor the one frame period of the video data.

Subsequently, the control unit 98 determines whether or not the horizontal synchronization signal detection unit 941 has detected the horizontal synchronization signal from the video data transmitted from the first camera head 5A. When the control unit 98 determines that the horizontal synchronization signal detection unit 941 has detected the horizontal synchronization signal from the video data transmitted from the first camera head 5A (step S206: Yes), the control device 9 proceeds to a step S207. On the other hand, when the control unit 98 determines that the horizontal synchronization signal detection unit 941 has not detected the horizontal synchronization signal from the video data transmitted from the first camera head 5A (step S206: No), the control device 9 continues this determination until the horizontal synchronization signal detection unit 941 detects the horizontal synchronization signal from the video data.

The monitoring unit 96 determines whether or not an abnormality occurs in the one frame period of the video data (step S207) based on the timing of the horizontal synchronization signal detected by the horizontal synchronization signal detection unit 941 in the step S204 and the timing of the horizontal synchronization signal detected by the horizontal synchronization signal detection unit 941 in the step S206. Specifically, the monitoring unit 96 determines whether or not the time, based on the rising timing of the horizontal synchronization signal detected by the horizontal synchronization signal detection unit 941 in the step S204 and the rising timing of the horizontal synchronization signal detected by the horizontal synchronization signal detection unit 941 in the step S206, is shorter or longer than a predetermined time (e.g., the time of the one field period ±10%), thereby determining whether or not an abnormality occurs in the one frame period. When the monitoring unit 96 determines that an abnormality occurs in the one frame period of the video data (step S207: Yes), the control device 9 proceeds to a step S208 described later. On the other hand, when the monitoring unit 96 determines that no abnormality occurs in the one frame period of the video data (step S207: No), the control device 9 proceeds to a step S209 described later.

In the step S208, the control unit 98 causes the display device 7 to display a warning that an abnormality occurs in the first camera head 5A.

Subsequently, the control unit 98 determines whether or not an instruction signal for ending the examination of the subject is input via the input unit 99 (step S209). When the control unit 98 determines that an instruction signal for ending the examination of the subject is input (step S209: Yes), the control device 9 returns to the main routine of FIG. 8 and ends the present processing. On the other hand, when the control unit 98 determines that an instruction signal for ending the examination of the subject is not input (step S209: No), the control device 9 returns to the step S205 described above.

Second Monitoring Processing

Figure 10:
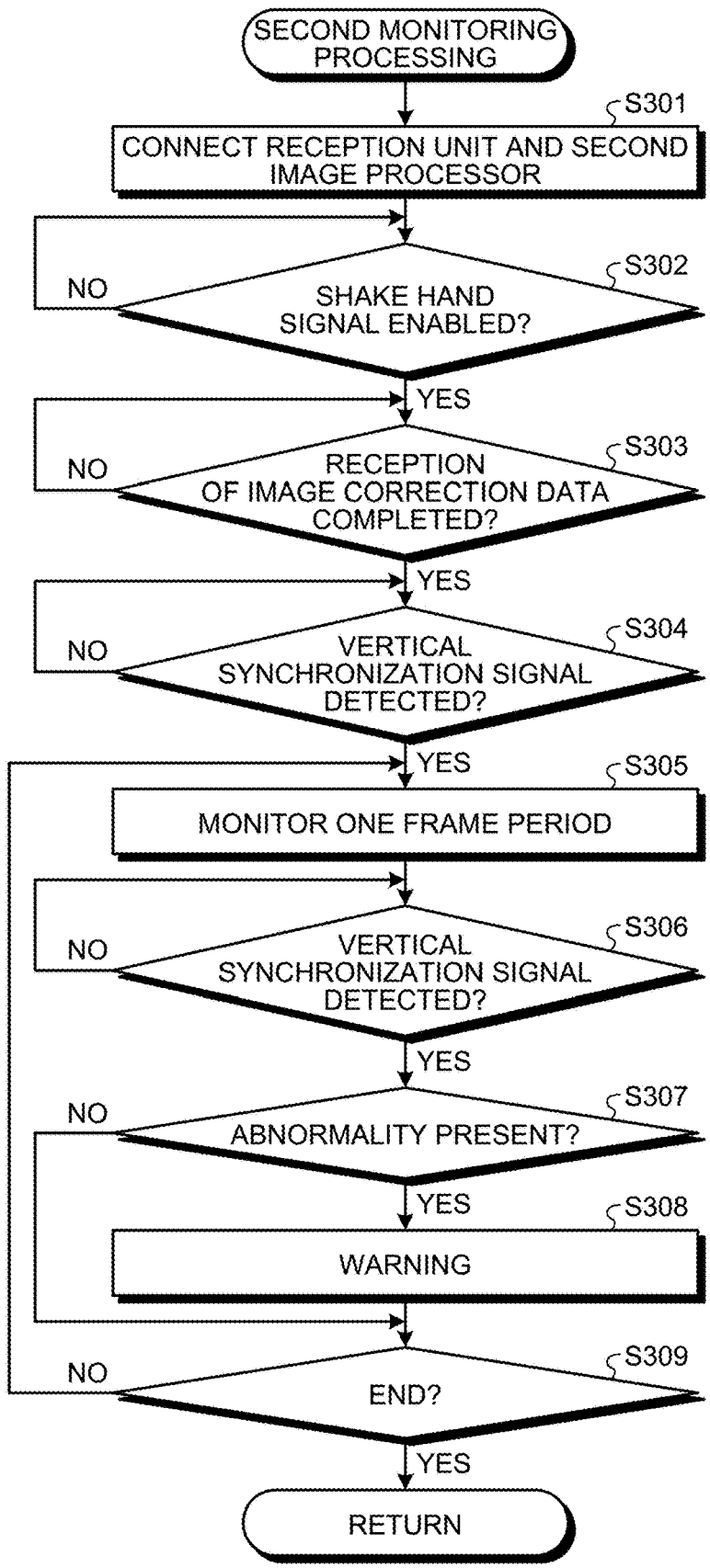
FIG. 10 is a flowchart indicating an outline of second monitoring processing of FIG. 8.

Next, details of the second monitoring processing described in the step S104 of FIG. 8 will be described. FIG. 10 is a flowchart indicating an outline of the second monitoring processing. Note that in FIG. 10, processing when the second camera head 5B is connected to the control device 9 will be described.

As illustrated in FIG. 10, the control unit 98 first connects the reception unit 92 and the second image processor 95 by controlling the switching unit 93 (step S301).

Subsequently, the control unit 98 determines based on the shake hand signal included in the video data output from the reception unit 92 whether or not the shake hand signal is enabled (step S302). When the control unit 98 determines that the shake hand signal is enabled (step S302: Yes), the control device 9 proceeds to a step S303 described later. On the other hand, when the control unit 98 determines that the shake hand signal is not enabled (step S302: No), the control device 9 continues this determination until the shake hand signal is enabled.

In the step S303, the control unit 98 determines based on the video data output from the reception unit 92 whether or not reception of the image correction data from the second camera head 5B included in the video data is completed. When the control unit 98 determines that the reception of the image correction data from the second camera head 5B included in the video data is completed (step S303: Yes), the control device 9 proceeds to a step S304 described later. On the other hand, when the control unit 98 determines that the reception of the image correction data from the second camera head 5B included in the video data is not completed (step S303: No), the control device 9 continues this determination until the reception of the image correction data is completed.

In the step S304, the control unit 98 determines whether or not the vertical synchronization signal detection unit 951 has detected the vertical synchronization signal from the video data transmitted from the second camera head 5B. When the control unit 98 determines that the vertical synchronization signal detection unit 951 has detected the vertical synchronization signal from the video data transmitted from the second camera head 5B (step S304: Yes), the control device 9 proceeds to a step S305. On the other hand, when the control unit 98 determines that the vertical synchronization signal detection unit 951 has not detected the vertical synchronization signal from the video data transmitted from the second camera head 5B (step S304: No), the control device 9 continues this determination until the vertical synchronization signal detection unit 951 detects the vertical synchronization signal from the video data.

In the step S305, the control unit 98 causes the monitoring unit 96 to monitor the one frame period of the video data.

Subsequently, the control unit 98 determines whether or not the vertical synchronization signal detection unit 951 has detected the vertical synchronization signal from the video data transmitted from the second camera head 5B. When the control unit 98 determines that the vertical synchronization signal detection unit 951 has detected the vertical synchronization signal from the video data transmitted from the second camera head 5B (step S306: Yes), the control device 9 proceeds to a step S307. On the other hand, when the control unit 98 determines that the vertical synchronization signal detection unit 951 has not detected the vertical synchronization signal from the video data transmitted from the second camera head 5B (step S306: No), the control device 9 continues this determination until the vertical synchronization signal detection unit 951 detects the vertical synchronization signal from the video data.

The monitoring unit 96 determines whether or not an abnormality occurs in the one frame period of the video data (step S307) based on the timing of the vertical synchronization signal detected by the vertical synchronization signal detection unit 951 in the step S304 and the timing of the vertical synchronization signal detected by the vertical synchronization signal detection unit 951 in the step S306. Specifically, the monitoring unit 96 determines whether or not the time, based on the rising timing of the vertical synchronization signal detected by the vertical synchronization signal detection unit 951 in the step S304 and the rising timing of the vertical synchronization signal detected by the vertical synchronization signal detection unit 951 in the step S306, is shorter or longer than a predetermined time (e.g., the time of the one field period ±10%), thereby determining whether or not an abnormality occurs in the one frame period of the video data. When the monitoring unit 96 determines that an abnormality occurs in the one frame period of the video data (step S307: Yes), the control device 9 proceeds to a step S308 described later. On the other hand, when the monitoring unit 96 determines that no abnormality occurs in the one frame period of the video data (Step S307: No), the control device 9 proceeds to a step S309 described later.

In the step S308, the control unit 98 causes the display device 7 to display a warning that an abnormality occurs in the second camera head 5B.

Subsequently, the control unit 98 determines whether or not an instruction signal for ending the examination of the subject is input via the input unit 99 (step S309). When the control unit 98 determines that an instruction signal for ending the examination of the subject is input (step S309: Yes), the control device 9 returns to the main routine of FIG. 8 and ends the present processing. On the other hand, when the control unit 98 determines that an instruction signal for ending the examination of the subject is not input (step S309: No), the control device 9 returns to the step S305 described above.

According to the first embodiment described above, the monitoring unit 96 monitors whether or not an abnormality occurs in the one frame period of the video data based on the period of the horizontal synchronization signal detected by the horizontal synchronization signal detection unit 941 for a predetermined n-th time after the polarity of the field signal is switched. As a result, a periodic disturbance of the one frame of the video data may be monitored regardless of the type of the camera head 5 (medical imaging device).

In addition, according to the first embodiment, the monitoring unit 96 monitors whether or not an abnormality occurs in the one frame period based on the period of the horizontal synchronization signal detected by the horizontal synchronization signal detection unit 941 for the first time immediately after the polarity of the field signal is switched. Therefore, a periodic disturbance of the one frame of the video data may be monitored regardless of the type of the camera head 5 (medical imaging device).

In addition, according to the first embodiment, the control unit 98 acquires an identification signal (identification information) for identifying the type of the camera head 5, and determines based on the identification signal whether or not the vertical synchronization signal is included in the video data. When the vertical synchronization signal is not included in the video data output from the camera head 5, the control unit 98 causes the switching unit 93 to connect the reception unit 92 and the first image processor 94, thereby causing the switching unit 93 to output the video data to the horizontal synchronization signal detection unit 941 of the first image processor 94. On the other hand, when the vertical synchronization signal is included in the video data output from the camera head 5, the control unit 98 causes the switching unit 93 to connect the reception unit 92 and the second image processor 95, thereby causing the switching unit 93 to output the video data to the vertical synchronization signal detection unit 951 of the second image processor 95. As a result, a periodic disturbance of the one frame of the video data may be monitored regardless of the type of the camera head 5 (medical imaging device), that is, of the first camera head 5A or the second camera head 5B.

In addition, according to the first embodiment, when the horizontal synchronization signal detection unit 941 detects the horizontal synchronization signal in a case where: the control unit 98 detects switching of the polarity of each of the shake hand signal and the field signal from the video data output from the camera head 5; and the control unit 98 detects the switching of the field signal after the shake hand signal is detected from the video data, the control unit 98 causes the monitoring unit 96 to monitor the one frame period of the video data. On the other hand, when the vertical synchronization signal detection unit 951 detects the vertical synchronization signal after the shake hand signal is detected from the video data, the control unit 98 causes the monitoring unit 96 to monitor the one frame period of the video data. As a result, a periodic disturbance of the one frame of the video data may be monitored regardless of the type of the camera head 5 (medical imaging device), that is, of the first camera head 5A or the second camera head 5B.

Second Embodiment

Next, a second embodiment will be described. In the first embodiment described above, a case where the present disclosure is applied to a rigid endoscope system using a rigid endoscope has been described. In the second embodiment, a case where the present disclosure is applied to a flexible endoscope system using a flexible endoscope will be described. Note that the same configurations as those of the endoscope system 1 according to the first embodiment described above will be denoted by the same reference numerals, and detailed description thereof will be omitted.

Schematic Configuration of Endoscope System

Figure 11:
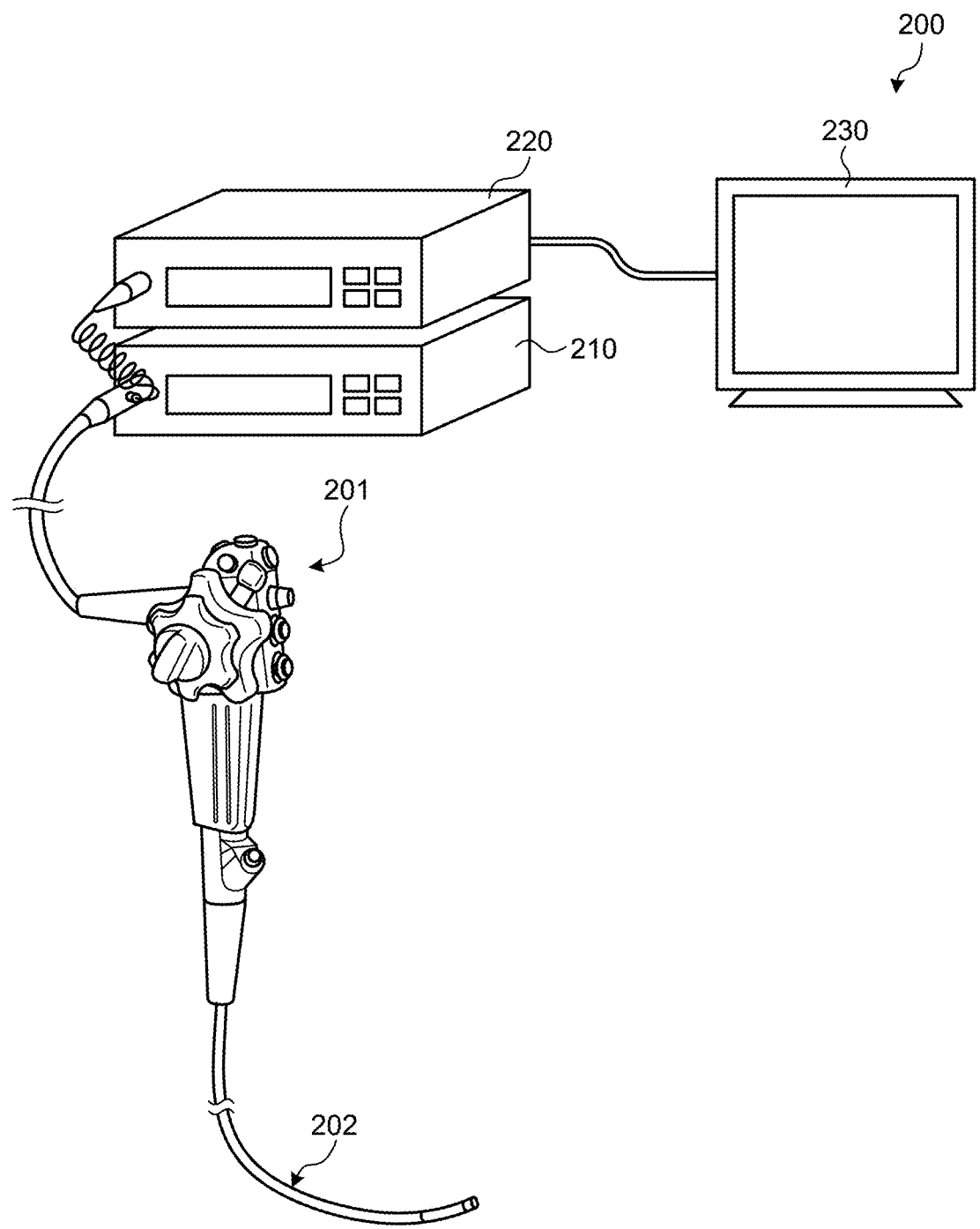
FIG. 11 is a view illustrating a schematic configuration of an endoscope system according to a second embodiment.

FIG. 11 is a view illustrating a schematic configuration of an endoscope system according to the second embodiment. An endoscope system 200 illustrated in FIG. 11 includes an endoscope 201 that captures an in-vivo image of an observed region by inserting an insertion unit 202 into a subject and generates video data, a light source device 210 that supplies white light or infrared light to the endoscope 201, a control device 220 that performs predetermined image processing on an image signal acquired by the endoscope 201 and comprehensively controls the entire operation of the endoscope system 200, and a display device 230 that displays the in-vivo image that the control device 220 has performed the image processing on.

The control device 220 includes at least the generation unit 91, the reception unit 92, the switching unit 93, the first image processor 94, the second image processor 95, the monitoring unit 96, the recording unit 97, the control unit 98, and the input unit 99 that have been described above.

According to the second embodiment described above, even the flexible endoscope system 200 may obtain the same effects as those of the first embodiment described above.

Third Embodiment

Next, a third embodiment will be described. In the first and second embodiments described above, the present disclosure is applied to an endoscope system. In the third embodiment, a case where the present disclosure is applied to a surgical microscope system will be described. Note that the same configurations as those of the endoscope system 1 according to the first embodiment described above will be denoted by the same reference numerals, and detailed description thereof will be omitted.

Configuration of Surgical Microscope System

Figure 12:
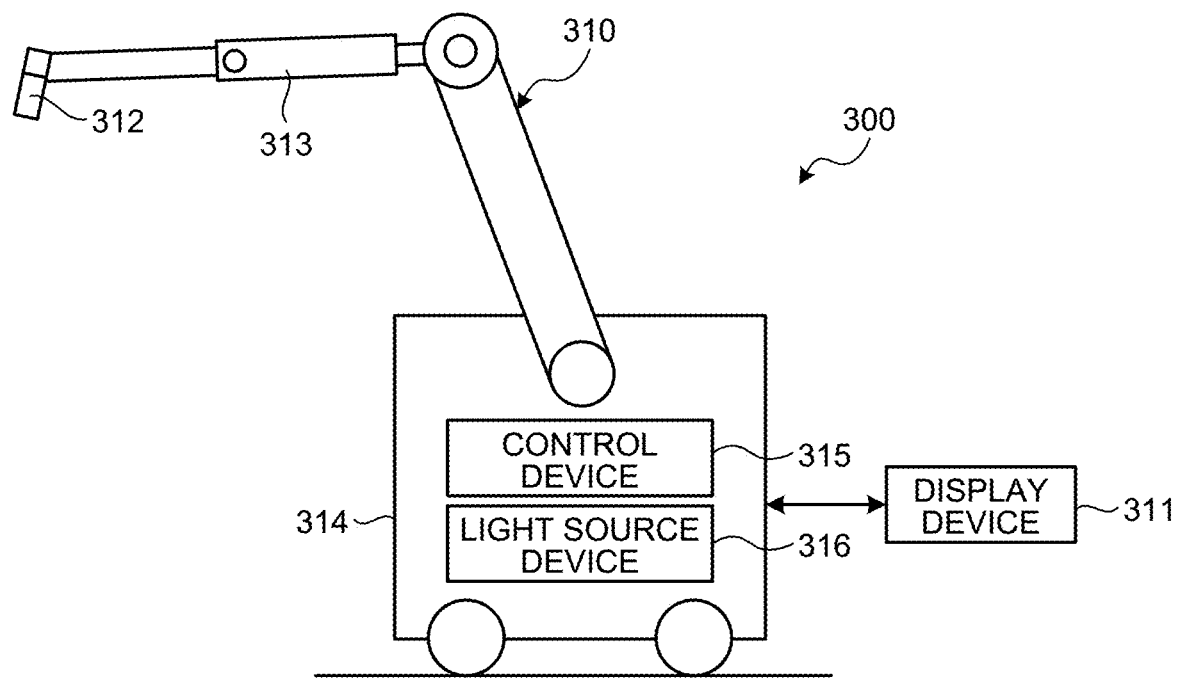
FIG. 12 is a view illustrating a schematic configuration of a surgical microscope system according to a third embodiment.

FIG. 12 is a view illustrating a schematic configuration of a surgical microscope system according to the third embodiment. A surgical microscope system 300 illustrated in FIG. 12 includes a microscope device 310 that is a medical imaging device that captures and acquires an image for observing a subject, and a display device 311 that displays video data captured by the microscope device 310. Note that the display device 311 and the microscope device 310 may also be integrally configured.

The microscope device 310 has a microscope unit 312 that enlarges and images a minute portion of a subject, a support unit 313 that is connected to a proximal end portion of the microscope unit 312 and includes an arm that rotatably supports the microscope unit 312, and a base unit 314 that rotatably holds a proximal end portion of the support unit 313 and is movable on a floor surface. The base unit 314 has a control device 315 that controls the operation of the surgical microscope system 300, and a light source device 316 that generates white light, infrared light, or the like to be emitted from the microscope device 310 to a subject. Note that the control device 315 has at least the generation unit 91, the reception unit 92, the switching unit 93, the first image processor 94, the second image processor 95, the monitoring unit 96, the recording unit 97, the control unit 98, and the input unit 99 that have been described above. Alternatively, the base unit 314 may be configured to support the support unit 313 by being fixed to a ceiling, a wall surface, or the like, not being provided to be movable on a floor surface.

The microscope unit 312 has, for example, a columnar shape. A switch that receives an input of an operation instruction for the microscope device 310 is provided on a side surface of the microscope unit 312. A cover glass (not illustrated) for protecting the inside is provided on an aperture surface of a lower end portion of the microscope unit 312.

In the surgical microscope system 300 configured as described above, a user such as an operator moves the microscope unit 312, performs a zoom operation, or switches illumination light while operating various switches in a state of grasping the microscope unit 312. Note that the shape of the microscope unit 312 is preferably a shape elongated in an observation direction such that the user may easily change a viewing direction by grasping it. Therefore, the shape of the microscope unit 312 may be a shape other than a columnar shape, and may be, for example, a polygonal columnar shape.

According to the third embodiment described above, even the surgical microscope system 300 may obtain the same effects as those of the first embodiment described above.

Other Embodiments

Variations may be formed by appropriately combining a plurality of components disclosed in the medical observation system according to an embodiment of the present disclosure described above. For example, some components may be removed from all the components described in the medical observation system according to the first embodiment of the present disclosure described above. Furthermore, the components described in the medical observation system according to the first embodiment of the present disclosure described above may be appropriately combined.

In addition, in the medical observation system according to the first embodiment of the present disclosure, the "unit" described above may be replaced with "means", "circuit", or the like. For example, the control unit may be replaced with control means or a control circuit.

In addition, the program to be executed by the medical observation system according to the first embodiment of the present disclosure is provided by being recorded, as file data in an installable format or an executable format, in a computer-readable recording medium such as a CD-ROM, a flexible disk (FD), a CD-R, a digital versatile disk (DVD), a USB medium, or a flash memory.

In addition, the program to be executed by the medical observation system according to the first embodiment of the present disclosure may be configured to be stored on a computer connected to a network such as the Internet and provided by being downloaded via the network.

Note that in the description of the flowcharts in the present specification, the context of processing between steps is clearly specified using expressions such as "first", "thereafter", and "subsequently". However, the orders of processing necessary for implementing the present disclosure are not uniquely determined by these expressions. That is, the orders of processing in the flowcharts described in the present specification may be changed as long as there is no contradiction.

Although some of the embodiments of the present application have been described in detail with reference to the drawings, these are merely examples, and the present disclosure may be implemented in other forms to which various modifications and improvements have been made based on the knowledge of those skilled in the art, including the aspects described in the section of the present disclosure. Note that the present technology may also have the following configurations.

(Supplementary Note 1)

A control device including:
  a generation unit that outputs a field signal to a medical imaging device;
  a first detection unit that detects a horizontal synchronization signal from video data that is output from the medical imaging device and includes at least the horizontal synchronization signal; and a monitoring unit that monitors whether or not an abnormality occurs in one frame period of the video data based on a period of the horizontal synchronization signal detected by the first detection unit for a predetermined n-th time after polarity of the field signal is switched.

(Supplementary Note 2)

The control device according to (Supplementary Note 1), in which the monitoring unit monitors whether or not an abnormality occurs in the one frame period based on a period of the horizontal synchronization signal detected by the first detection unit for the first time immediately after the polarity of the field signal is switched.

(Supplementary Note 3)

The control device according to (Supplementary Note 1) or (Supplementary Note 2), including:

a second detection unit that detects a vertical synchronization signal;

a switching unit that outputs the video data to the first detection unit or the second detection unit; and a control unit that: acquires an identification signal for identifying a type of the medical imaging device; determines based on the identification signal whether or not the vertical synchronization signal is included in the video data; causes the switching unit to output the video data to the first detection unit when the vertical synchronization signal is not included in the video data; and on the other hand, causes the switching unit to output the video data to the second detection unit when the vertical synchronization signal is included in the video data.

(Supplementary Note 4)

The control device according to (Supplementary Note 3), in which the medical imaging device includes a first image sensor capable of outputting the video data including the horizontal synchronization signal or a second image sensor capable of outputting the video data including the vertical synchronization signal, the identification signal includes information for identifying the first image sensor or the second image sensor, and the control unit causes, based on the identification signal, the switching unit to output the video data to the first detection unit when the medical imaging device includes the first image sensor, and, on the other hand, causes the switching unit to output the video data to the second detection unit when the medical imaging device includes the second image sensor.

(Supplementary Note 5)

The control device according to (Supplementary Note 3) or (Supplementary Note 4), in which when the second detection unit detects the vertical synchronization signal, the monitoring unit monitors, based on the vertical synchronization signal, whether or not an abnormality occurs in the one frame period.

(Supplementary Note 6)

The control device according to any one of (Supplementary Note 3) to (Supplementary Note 5), in which the video data further includes a shake hand signal that indicates that communication between the medical imaging device and the control device is established, and the control unit detects switching of polarity of each of the shake hand signal and the field signal from the video data, causes, in a case where the control unit detects the switching of the polarity of the field signal after the shake hand signal is detected, the monitoring unit to monitor the one frame period when the first detection unit detects the horizontal synchronization signal, and, on the other hand, causes the monitoring unit to monitor the one frame period when the second detection unit detects the vertical synchronization signal after the shake hand signal is detected.

(Supplementary Note 7)

The control device according to any one of (Supplementary Note 1) to (Supplementary Note 6), in which the medical imaging device is an endoscope or a surgical microscope device.

(Supplementary Note 8)

A medical observation system including:

a medical imaging device that images a subject and outputs video data; and a control device to which the medical imaging device may be connected, in which the control device includes:

a generation unit that outputs a field signal to the medical imaging device;

a first detection unit that detects a horizontal synchronization signal from video data that is output from the medical imaging device and includes at least the horizontal synchronization signal; and a monitoring unit that monitors whether or not an abnormality occurs in one frame period of the video data based on a period of the horizontal synchronization signal detected by the first detection unit for a predetermined n-th time after polarity of the field signal is switched.

(Supplementary Note 9)

A control method executed by a control device that includes a processor having hardware and to which a medical imaging device is connected, the control method including:

outputting a field signal to the medical imaging device;

detecting a horizontal synchronization signal from video data that is output from the medical imaging device and includes at least the horizontal synchronization signal; and monitoring whether or not an abnormality occurs in one frame period of the video data based on a period of the horizontal synchronization signal detected for a predetermined n-th time after polarity of the field signal is switched.

(Supplementary Note 10)

A program for causing a control device that includes a processor having hardware and to which a medical imaging device is connected, to:

output a field signal to the medical imaging device;

detect a horizontal synchronization signal from video data that is output from the medical imaging device and includes at least the horizontal synchronization signal; and monitor whether or not an abnormality occurs in one frame period of the video data based on a period of the horizontal synchronization signal detected for a predetermined n-th time after polarity of the field signal is switched.

What is claimed is:

1. A non-transitory computer-readable recording medium on which an executable program is recorded, the program causing a processor of a computer to execute:
   outputting a field signal to a medical imaging device;
   acquiring an identification signal for identifying a type of the medical imaging device;
   determining based on the identification signal whether or not a vertical synchronization signal is included in the video data;
   detecting a horizontal synchronization signal from video data output from the medical imaging device, the video data including at least the horizontal synchronization signal; and
   monitoring whether or not an abnormality occurs in one frame period of the video data based on a period of the horizontal synchronization signal detected for a predetermined n-th time after polarity of the field signal is switched.

2. The non-transitory computer-readable recording medium according to claim 1, wherein the processor is further configured to execute:
   outputting the video data to detecting the horizontal synchronization signal in a case where the vertical synchronization signal is not included in the video data; and
   outputting the video data to detecting the vertical synchronization signal in a case where a vertical synchronization signal is included in the video data.

3. The non-transitory computer-readable recording medium according to claim 1, wherein the medical imaging device is an endoscope or a surgical microscope device.

4. A control device comprising:
   generation circuitry configured to output a field signal to a medical imaging device;
   first detection circuitry configured to detect a horizontal synchronization signal from video data output from the medical imaging device, the video data including at least the horizontal synchronization signal;
   a monitoring circuitry configured to monitor whether or not an abnormality occurs in one frame period of the video data based on a period of the horizontal synchronization signal detected by the first detection circuitry for a predetermined n-th time after polarity of the field signal is switched; and
   a controller configured to:
      acquire an identification signal for identifying a type of the medical imaging device, and
      determine based on the identification signal whether or not a vertical synchronization signal is included in the video data.

5. The control device according to claim 4, comprising:
   a second detection circuitry configured to detect a vertical synchronization signal;
   a switching circuitry configured to output the video data to the first detection circuitry or to the second detection circuitry; wherein the controller is further configured to:
      cause the switching circuitry to output the video data to the first detection circuitry in a case where the vertical synchronization signal is not included in the video data; and
      cause the switching circuitry to output the video data to the second detection circuitry in a case where the vertical synchronization signal is included in the video data.

6. The control device according to claim 5, wherein
   the medical imaging device includes
      a first image sensor configured to output the video data including the horizontal synchronization signal, or
      a second image sensor configured to output the video data including the vertical synchronization signal,
   the identification signal includes information for identifying the first image sensor or the second image sensor, and
   the controller is configured to
      cause, based on the identifying information, the switching circuitry to output the video data to the first detection circuitry in a case where the medical imaging device includes the first image sensor, and
      cause the switching circuitry to output the video data to the second detection circuitry in a case where the medical imaging device includes the second image sensor.

7. The control device according to claim 5, wherein in a case where the second detection circuitry detects the vertical synchronization signal, the monitoring circuitry is configured to monitor, based on the vertical synchronization signal, whether or not an abnormality occurs in the one frame period.

8. The control device according to claim 5, wherein
   the video data further includes a shake hand signal that indicates that communication between the medical imaging device and the control device is established, and
   the controller is configured to
      detect switching of polarity of each of the shake hand signal and the field signal from the video data,
      cause, in a case where the controller detects the switching of the polarity of the field signal after the shake hand signal is detected, the monitoring circuitry to monitor the one frame period in a case where the first detection circuitry detects the horizontal synchronization signal, and,
      cause the monitoring circuitry to monitor the one frame period in a case where the second detection circuitry detects the vertical synchronization signal after the shake hand signal is detected.

9. The control device according to claim 4, wherein the medical imaging device is an endoscope or a surgical microscope device.

10. A medical observation system comprising:
   a medical imaging device configured to image a subject and outputs video data; and
   a control device configured to connect with the medical imaging device, the control device including:
      a generation circuitry configured to output a field signal to the medical imaging device;
      a first detection circuitry configured to detect a horizontal synchronization signal from video data output from the medical imaging device, the video data including at least the horizontal synchronization signal;
      a monitoring circuitry configured to monitor whether or not an abnormality occurs in one frame period of the video data based on a period of the horizontal synchronization signal detected by the first detection circuitry for a predetermined n-th time after polarity of the field signal is switched; and a controller configured to
  acquire an identification signal for identifying a type of the medical imaging, device, and
  determine based on the identification signal whether or not a vertical synchronization signal is included in the video data.

11. The medical observation system according to claim 10, wherein the control device further includes:
a second detection circuitry configured to detect a vertical synchronization signal;
a switching circuitry configured to output the video data to the first detection circuitry or to the second detection circuitry; and
the controller is configured to:
  cause the switching circuitry to output the video data to the first detection circuitry in a case where the vertical synchronization signal is not included in the video data; and
  cause the switching circuitry to output the video data to the second detection circuitry in a case where the vertical synchronization signal is included in the video data.

12. The medical observation system according to claim 10, wherein the medical imaging device is an endoscope or a surgical microscope device.

13. A control method executed by a control device that includes a processor having hardware and to which a medical imaging device is connected, the control method comprising:

outputting a field signal to the medical imaging device;
acquiring an identification signal for identifying a type of the medical imaging device;
determining based on the identification signal whether or not a vertical synchronization signal is included in the video data;
detecting a horizontal synchronization signal from video data output from the medical imaging device, the video data including at least the horizontal synchronization signal; and
monitoring whether or not an abnormality occurs in one frame period of the video data based on a period of the horizontal synchronization signal detected for a predetermined n-th time after polarity of the field signal is switched.

14. The control method according to claim 13, further comprising:
outputting the video data to detecting the horizontal synchronization signal in a case where the vertical synchronization signal is not included in the video data; and
outputting the video data to the detecting the vertical synchronization signal in a case where the vertical synchronization signal is included in the video data.

15. The control method according to claim 13, wherein the medical imaging device is an endoscope or a surgical microscope device.

* * * * *